(12) United States Patent
Chang et al.

(10) Patent No.: US 11,006,858 B2
(45) Date of Patent: May 18, 2021

(54) TEETH MOVEMENT TRACKING DEVICE AND METHOD THEREOF

(71) Applicant: MEDIT CORP., Seoul (KR)

(72) Inventors: Minho Chang, Seoul (KR); Soobok Lee, Seoul (KR); Jiwoong Chang, Seoul (KR); Sungbin Im, Seoul (KR)

(73) Assignee: MEDIT CORP., Seoul (KR)

( * ) Notice: Subject to any disclaimer, the term of this patent is extended or adjusted under 35 U.S.C. 154(b) by 49 days.

(21) Appl. No.: 16/098,942

(22) PCT Filed: Nov. 24, 2016

(86) PCT No.: PCT/KR2016/013635
§ 371 (c)(1),
(2) Date: Nov. 5, 2018

(87) PCT Pub. No.: WO2017/191878
PCT Pub. Date: Nov. 9, 2017

(65) Prior Publication Data
US 2019/0090784 A1    Mar. 28, 2019

(30) Foreign Application Priority Data
May 4, 2016  (KR) ........................ 10-2016-0055612

(51) Int. Cl.
*A61B 5/11*  (2006.01)
*G06T 5/00*  (2006.01)
(Continued)

(52) U.S. Cl.
CPC ........... *A61B 5/1111* (2013.01); *A61B 5/1122* (2013.01); *A61B 5/1128* (2013.01);
(Continued)

(58) Field of Classification Search
CPC ... A61B 5/1111; A61B 5/1122; A61B 5/1128; G06T 17/00; G06T 2207/30036; G06T 2207/30204; G06T 2207/30241
See application file for complete search history.

(56) References Cited

U.S. PATENT DOCUMENTS

2005/0277086 A1*  12/2005  Arai ................... A61C 19/045
                                                             433/54
2007/0207441 A1*   9/2007  Lauren ............... A61C 13/0004
                                                             433/213
(Continued)

FOREIGN PATENT DOCUMENTS

JP    3855038 B2    12/2006
JP    5495415 B2     5/2014
(Continued)

OTHER PUBLICATIONS

International Search Report for PCT/KR2016/013635 dated Feb. 27, 2017 from Korean Intellectual Property Office.
(Continued)

*Primary Examiner* — David Bilodeau
(74) *Attorney, Agent, or Firm* — Paratus Law Group, PLLC (57) ABSTRACT

A teeth movement tracking device, including: an input unit for receiving three-dimensional teeth data and image data having the shape of teeth; an image processing unit for combining the three-dimensional teeth data with the image data; a movement tracking unit for detecting the axis of rotation with respect to the rotation of the teeth or temporomandibular joint by analyzing the image data or the three-dimensional teeth data; and a trajectory generation unit for calculating the movement trajectory of the teeth or the temporomandibular joint by analyzing the image data or the three-dimensional teeth data.

9 Claims, 10 Drawing Sheets

(51) Int. Cl.
*G06T 7/00* (2017.01)
*G06T 17/00* (2006.01)
*A61C 9/00* (2006.01)
*A61C 7/00* (2006.01)
*A61C 19/04* (2006.01)
*G06T 7/246* (2017.01)

(52) U.S. Cl.
CPC ............... *A61C 7/00* (2013.01); *A61C 9/00* (2013.01); *A61C 9/0046* (2013.01); *A61C 19/04* (2013.01); *G06T 5/00* (2013.01); *G06T 7/00* (2013.01); *G06T 7/0012* (2013.01); *G06T 7/251* (2017.01); *G06T 17/00* (2013.01); *G06T 2207/30036* (2013.01); *G06T 2207/30204* (2013.01); *G06T 2207/30241* (2013.01)

(56) References Cited

U.S. PATENT DOCUMENTS

| | | | | |
|---|---|---|---|---|
| 2011/0038519 | A1* | 2/2011 | Nakai | A61B 6/032 382/131 |
| 2011/0102549 | A1* | 5/2011 | Takahashi | A61C 1/084 348/46 |
| 2011/0194787 | A1* | 8/2011 | Chun | G06T 7/50 382/284 |
| 2011/0218426 | A1* | 9/2011 | Shinjo | A61B 5/1111 600/425 |
| 2012/0015316 | A1* | 1/2012 | Sachdeva | G06T 17/00 433/24 |
| 2013/0066598 | A1* | 3/2013 | Fisker | A61C 11/00 703/1 |
| 2013/0151208 | A1* | 6/2013 | Ito | A61C 7/002 703/1 |
| 2015/0289960 | A1* | 10/2015 | Shigemoto | A61B 5/1077 433/27 |
| 2016/0128624 | A1* | 5/2016 | Matt | A61C 19/045 600/301 |
| 2016/0135925 | A1* | 5/2016 | Mason | A61C 7/08 703/2 |
| 2017/0143445 | A1* | 5/2017 | Abkai | A61B 90/39 |
| 2017/0325909 | A1* | 11/2017 | Gao | A61C 7/002 |
| 2018/0005377 | A1* | 1/2018 | Alvarez | A61C 9/0053 |
| 2019/0147591 | A1* | 5/2019 | Chang | A61B 6/14 382/128 |
| 2019/0290408 | A1* | 9/2019 | Fisker | A61C 19/05 |

FOREIGN PATENT DOCUMENTS

| | | |
|---|---|---|
| KR | 10-0954552 B1 | 4/2010 |
| KR | 10-2011-0100141 A | 9/2011 |
| KR | 10-1189550 B1 | 10/2012 |
| KR | 10-2015-0082428 A | 7/2015 |
| WO | WO 2007/130573 A2 | 11/2007 |

OTHER PUBLICATIONS

Extended European Search Report for related EP application No. 16901104.6 dated Dec. 11, 2019 from European Patent Office.
Sung-Goo Kim et al, "The relationship between three-dimensional principal rotations and mandibular deviation", OOOOE, Nov. 2010, pp. 52-60, vol. 110, No. 5.

\* cited by examiner

TEETH MOVEMENT TRACKING DEVICE AND METHOD THEREOF

CROSS REFERENCE TO PRIOR APPLICATIONS

This application is a National Stage Patent Application of PCT International Patent Application No. PCT/KR2016/013635 (filed on Nov. 24, 2016) under 35 U.S.C. § 371, which claims priority to Korean Patent Application No. 10-2016-0055612 (filed on May 4, 2016), which are all hereby incorporated by reference in their entirety.

BACKGROUND

The present disclosure relates to a teeth movement tracking device and a method thereof, and more particularly, to a teeth movement tracking device for detecting the movement of teeth to extract the movement trajectory of the teeth or temporomandibular joint and a method thereof.

Generally, teeth of a person are connected to temporomandibular joint to have complicated movement according to the degree and direction of the movement of the temporomandibular joint.

Particularly, it is necessary to evaluate the masticatory ability of a person, to confirm whether or not there is abnormal in the temporomandibular joint disease, and to confirm how much the teeth or the temporomandibular joint are deviated from the normal movement in order to determine the state of the teeth or the temporomandibular joint.

However, the movement of the temporomandibular joint of a person is not only very complicated but also the movement thereof is not exposed to the outside, such that it is very difficult to track the movement trajectory thereof only with appearance simply.

For this purpose, conventionally, in order to diagnose a person who has a problem in the temporomandibular joint, the shape of a jawbone has been photographed using a device such as a CT or a MRI.

However, although such a device can photograph the shape of the temporomandibular joint, there is a problem in that it is not possible to measure the movement of the temporomandibular joint because it should not be moved during the measurement. The movement thereof has not been tracked because the moving temporomandibular joint could not be photographed.

Meanwhile, Korean Patent Publication No. 10-2015-0082428 (published on Jul. 15, 2015) is disclosed as the related art of a technology for estimating the movement trajectory from a specific scan to a next scan through three-dimensional scan within an oral cavity and compensating for the movement trajectory.

SUMMARY

The present disclosure relates to a teeth movement tracking device and a method thereof, and more particularly, to a teeth movement tracking device and a method thereof, which combines teeth data with facial data of a moving person, detects a feature point to track the movement thereof, thus generating trajectory data according to the movement of teeth or temporomandibular joint.

A teeth movement tracking device in accordance with the present disclosure includes an input unit for receiving three-dimensional teeth data and image data having the shape of teeth; an image processing unit for combining the three-dimensional teeth data with the image data; a movement tracking unit for detecting the axis of rotation with respect to the rotation of the teeth or temporomandibular joint by analyzing the image data or the three-dimensional teeth data; and a trajectory generation unit for calculating the movement trajectory of the teeth or the temporomandibular joint by analyzing the image data or the three-dimensional teeth data.

In addition, the image processing unit can align the three-dimensional teeth data with the image data and synchronize the movement thereof.

In addition, the input unit can receive the image data having two or more continuity.

In addition, the image processing unit can convert all or part of the image data into three-dimensional data.

In addition, the three-dimensional data can be converted using a feature point or an attached target on the image data.

In addition, the movement tracking unit can detect the axis of rotation by analyzing the movement of the teeth data or the image data.

In addition, the movement tracking unit can detect the axis of rotation by determining the section having the least movement in the teeth data or the image data.

In addition, the trajectory generation unit can track the rotation or free motion of the teeth or the temporomandibular joint with respect to the axis of rotation detected by the movement tracking unit.

A teeth movement tracking method in accordance with another aspect of the present disclosure includes receiving three-dimensional teeth data and image data having the shape of teeth by scanning a face; combining the three-dimensional teeth data with the image data; detecting the axis of rotation with respect to the rotation of the teeth or temporomandibular joint by analyzing the image data or the three-dimensional teeth data; and calculating the movement trajectory of the teeth or the temporomandibular joint by analyzing the image data or the three-dimensional teeth data.

In addition, the receiving the image data can receive the image data having two or more continuity.

In addition, the combining the three-dimensional teeth data with the image data can align the three-dimensional teeth data with the image data and synchronize the movement thereof.

In addition, the combining the three-dimensional teeth data with the image data can further include converting all or part of the image data into three-dimensional data.

In addition, the three-dimensional data can be converted using a feature point or an attached target on the image data.

In addition, the detecting the axis of rotation can detect the axis of rotation by analyzing the movement of the teeth data or the image data.

In addition, the detecting the axis of rotation can detect the axis of rotation by determining the section having the least movement in the teeth data or the image data.

In addition, the calculating the movement trajectory can track the rotation or free motion of the teeth or the temporomandibular joint with respect to the detected axis of rotation.

The teeth movement tracking device and the method thereof in accordance with the present disclosure configured as described above can match the three-dimensional teeth data with the image data that scans the moving face, and then track the movement of the temporomandibular joint based on the moving face to generate the trajectory data, thus recording the movement of the teeth or the temporomandibular joint that is different for each person and tracking precise movement. As a result, it is possible to perform accurate diagnosis in diagnosis and treatment, and to be used for treatment of prosthesis, correction, and plastic surgery in post-treatment.

DETAILED DESCRIPTION

The advantages and features of the present disclosure and the method for achieving them will become apparent with reference to the embodiments described in detail below with reference to the accompanying drawings. The present disclosure can, however, be embodied in various forms and should not be construed as limited to the embodiments disclosed herein; these embodiments are only provided so that this disclosure will be thorough and complete and will fully convey the scope of the disclosure to those skilled in the art to which the present disclosure pertains; and the present disclosure is only defined by the scope of the claims. Like reference numerals refer to like elements throughout the specification.

Hereinafter, embodiments of the present disclosure will be described in detail with reference to the drawings.

Figure 1:
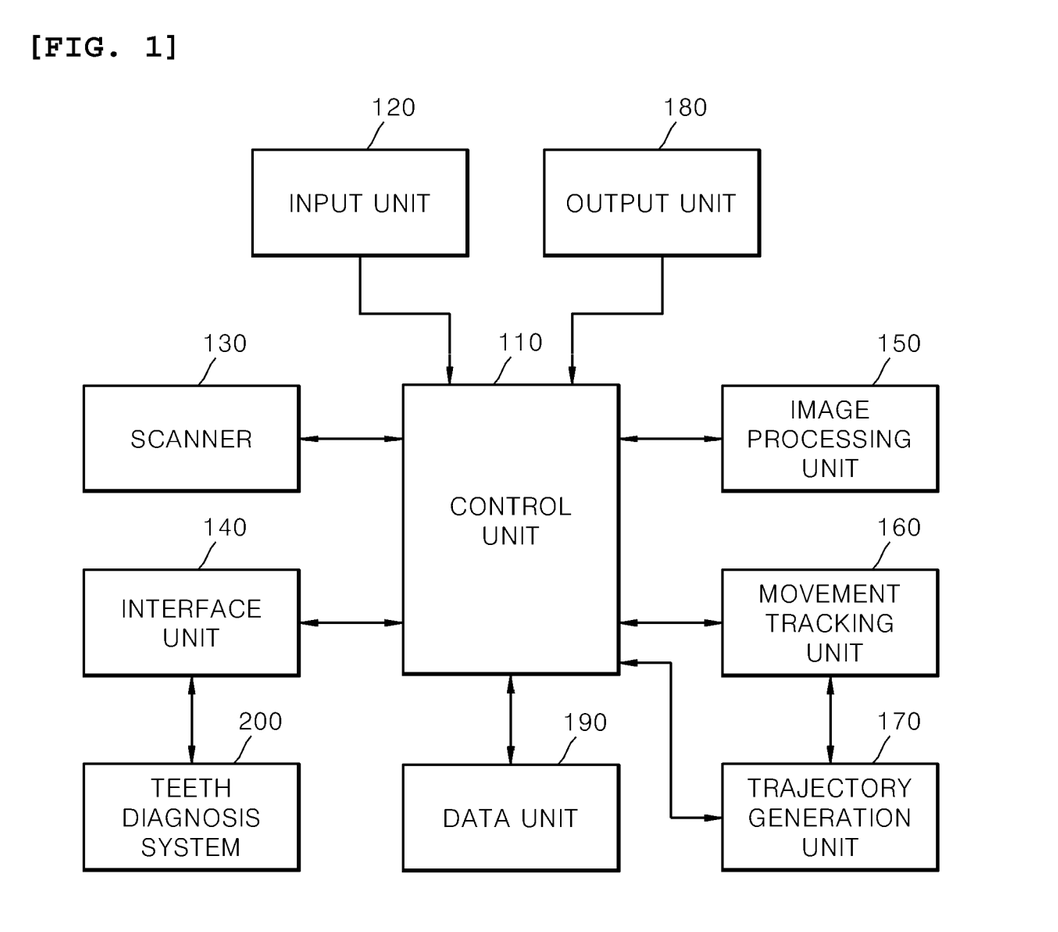
FIG. 1 is a block diagram schematically illustrating a configuration of a teeth movement tracking device in accordance with the present disclosure.

FIG. 1 is a block diagram schematically illustrating a configuration of a teeth movement tracking device in accordance with the present disclosure.

As illustrated in FIG. 1, a teeth movement tracking device in accordance with the present disclosure includes an input unit 120, an image processing unit 150, a movement tracking unit 160, a trajectory generation unit 170, a control unit 110, and a data unit 190. In addition, the teeth movement tracking device further includes an external server or another device, for example, an interface unit 140 for transmitting and receiving data with a teeth diagnosis system 200, etc. in FIG. 1.

The interface unit 140 receives teeth data from a connected device, and transmits trajectory data output from the trajectory generation unit 170 to the connected device. The interface unit is provided with a connection port and a wired/wireless communication module.

Herein, the teeth data are data having information on teeth of a person, and include data scanning teeth through a dental scanner, three-dimensional image data, or image data having the shape of the teeth measured by a Computed Tomography (CT) or a Magnetic Resonance Imaging (MRI).

The input unit 120 includes an input means such as at least one button, a switch, and a touch pad. The input unit 120 can receive a start or end command for tracking the movement of the teeth or the temporomandibular joint, and select and input a reference point for tracking the movement thereof.

The input unit 120 can receive the three-dimensional teeth data and the image data having the shape of the teeth as described above.

The scanner 130 can use a two-dimensional scanner or a three-dimensional scanner, and can also include a photographing means for photographing the movement. The scanner 130 scans successively and inputs an object in real time. For example, the scanner 130 can scan or photograph the face of a moving person by a moving picture to input it to the input unit 120 in real time, and can input two or more consecutive image data to the input unit 120 in real time.

The scanner 130 photographs or scans the face of the moving person such as masticatory motion through two-dimensional image processing in real time to input it to the input unit 120. While a person performs the masticatory motion, the face shape of the person is changed by the movement of the teeth or the temporomandibular joint.

The scanner 130 photographs or scans the moving face for a certain time to input it as image data.

The image processing unit 150 analyzes and converts the image data input from the scanner 130. Herein, the image processing unit 150 converts all or part of the input image data into three-dimensional data. Particularly, the image processing unit 150 can convert it into three-dimensional data using a feature point or an attached target on the image data. The feature point and the target will be described later.

The image processing unit 150 combines the input or received three-dimensional teeth data with the image data photographed through the scanner. Specifically, the image processing unit 150 generates three-dimensional coordinate by mapping the three-dimensional teeth data with the image data, thus generating three-dimensional moving data.

In this time, the image processing unit 150 can generate the three-dimensional coordinate at a high speed by mapping the input three-dimensional teeth data with the image data of the face. Herein, the image processing unit 150 aligns the teeth data with the image data and synchronizes the movement thereof.

In addition, when the target is included in the image data, the image processing unit 150 detects the target from the image data.

Meanwhile, the movement tracking unit 160 detects the axis of rotation with respect to the rotation of the teeth or the temporomandibular joint by analyzing the image data or the teeth data. Particularly, the movement tracking unit 160 detects the axis of rotation by analyzing the movement of the teeth data or the image data, and the movement tracking unit 160 detects the axis of rotation by determining the section having the least movement in the teeth data or the image data.

Specifically, the movement tracking unit 160 sets a plurality of feature points based on the three-dimensional data and tracks the movement of each feature point.

The movement tracking unit 160 detects the axis of rotation by comparing the movement of the respective feature points to determine a feature point having the least movement. Generally, when analyzing the motion of the temporomandibular joint that opens a mouth, the motion of the temporomandibular joint performs an initial rotation motion, and then after a certain section, performs the rotation motion with a straight-line motion (a linear motion). Accordingly, it is necessary to find the axis of rotation for the rotation motion of the temporomandibular joint in the section performing the initial rotation motion.

For this purpose, the movement tracking unit 160 detects the axis of rotation of the temporomandibular joint in the section of the rotation motion of the teeth through the image data of the face having the bottom of the teeth. As will be described later, the movement tracking unit 160 sets a plurality of feature points based on the three-dimensional data, tracks the movement of each feature point, and detects the axis of rotation by determining a feature point having the least movement among the respective feature points.

When the target is included in the image data, the movement tracking unit 160 determines the movement through the movement of the detected target.

In addition, the movement tracking unit 160 sets a reference point, detects the axis of rotation by comparing the distance between the feature points from the reference point, and detects the up and down motion and straight-line motion of the teeth or the temporomandibular joint.

Meanwhile, the trajectory generation unit 170 tracks the rotation or free motion of the teeth or the temporomandibular joint with respect to the axis of rotation detected by the movement tracking unit 160. Specifically, the trajectory generation unit 170 detects the feature of the axis of rotation of the temporomandibular joint, and the up and down motion and straight-line motion of the temporomandibular joint that are detected by the movement tracking unit 160.

The trajectory generation unit 170 finds the trajectory of the linear motion of the temporomandibular joint to generate trajectory data. The trajectory data are stored in the data unit 190.

The output unit 180 can include a display means for outputting and displaying data, and in addition, can further include a speaker or an operation lamp for outputting a progressing state and a warning sound.

The data unit 190 stores the data input through the input unit 120 or the scanner 130, and the data of the image processing unit 150 and the movement tracking unit 160, and stores the trajectory data of the trajectory generation unit 170.

Figure 2:
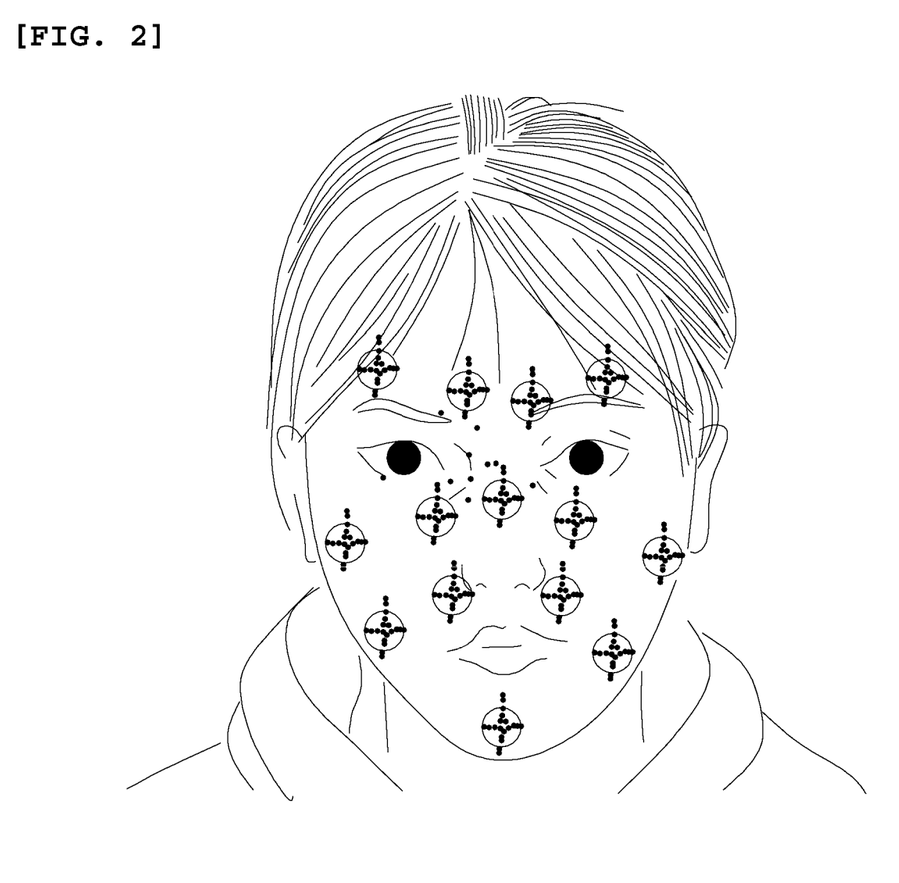
FIG. 2 is a diagram illustrating an example of movement information for tracking the movement of teeth or temporomandibular joint in accordance with the present disclosure.

FIG. 2 is a diagram illustrating an example of movement information for tracking the movement of the teeth or the temporomandibular joint in accordance with the present disclosure.

As illustrated in FIG. 2, a plurality of targets can be attached to the face of a person in order to scan a moving face.

When the target is attached to a plurality of locations of the face of the person to start scanning, the movement as the person speaks or chews food is scanned. The target also moves according to the movement of the face.

The image processing unit 150 extracts the target from the image data, and the movement tracking unit 160 detects the axis of rotation based on the moved target and extracts the direction and degree of the movement thereof.

Meanwhile, when there is no target on the face of the person, it can be processed by setting the feature point as described above.

Figure 3:
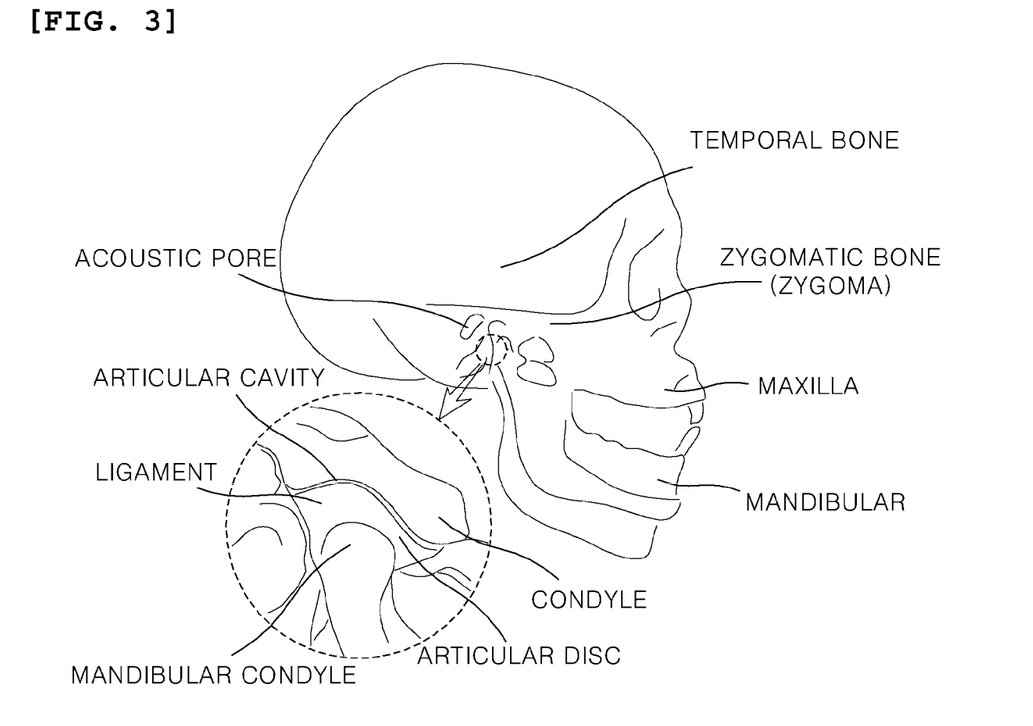
FIGS. 3 and 4 are diagrams for explaining a configuration of the temporomandibular joint and a method for tracking the movement thereof in accordance with the present disclosure.
Figure 4:
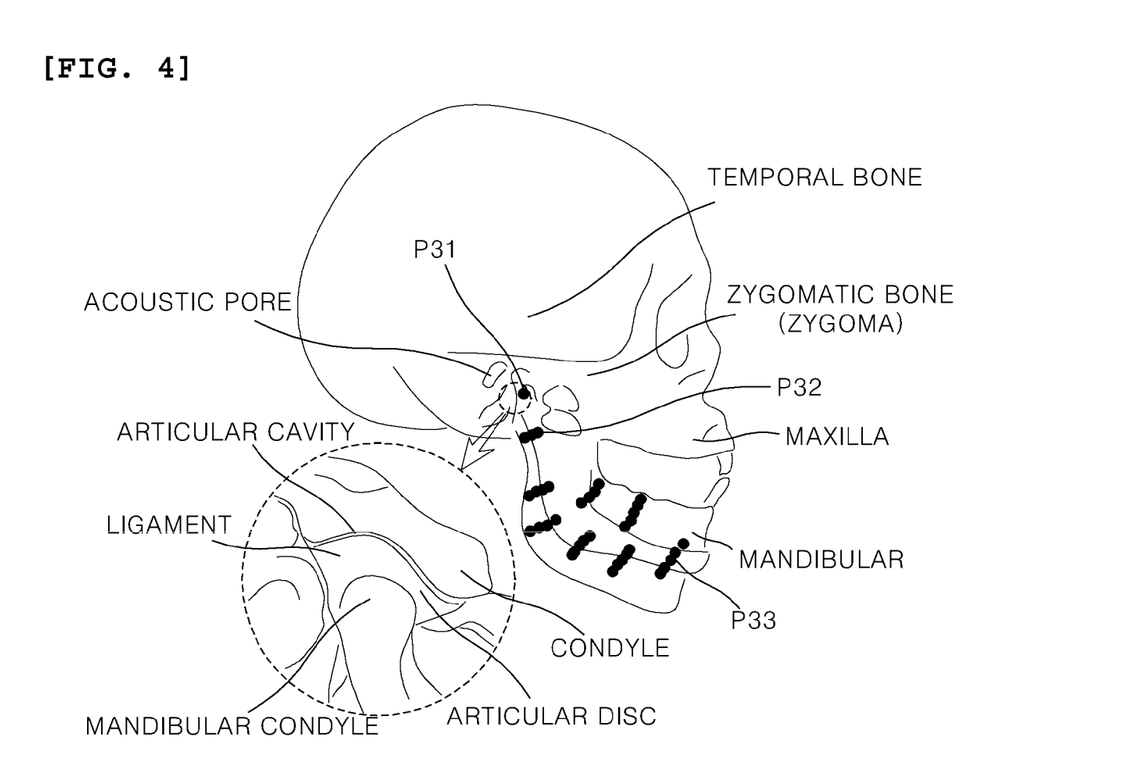

FIGS. 3 and 4 are diagrams for explaining a configuration of temporomandibular joint and a method for tracking the movement thereof in accordance with the present disclosure.

FIG. 3 illustrates teeth and temporomandibular joint in the skull of a person, and the teeth, which is divided into maxilla and mandible, moves through the movement of the temporomandibular joint to perform masticatory activity.

Accordingly, it is possible to track the movement of the teeth or the temporomandibular joint to generate trajectory data for the movement thereof so that the abnormality of the teeth or the temporomandibular joint can be diagnosed.

In this time, it is possible to set a plurality of feature points, to detect the axis of rotation by tracking the movement of the feature point according to the movement of the temporomandibular joint, and to generate the trajectory data thereof.

As illustrated in FIG. 4, when the temporomandibular joint is moved, the feature point corresponding thereto is moved to the lower end thereof, and the feature point having the least movement based on the moving degree thereof can be detected as the axis of rotation. For example, a P31 having the least movement among a plurality of feature points P31, P32, P33 can become the axis of rotation.

Figure 5:
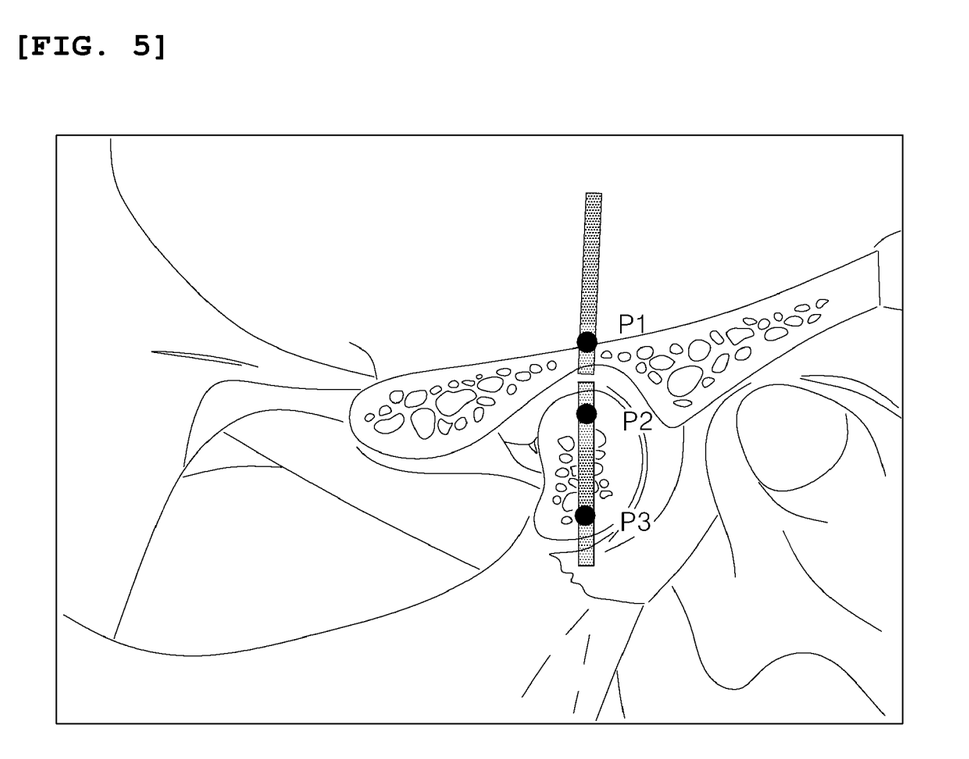
FIGS. 5 to 7 are exemplary diagrams for explaining the movement of the temporomandibular joint of the teeth movement tracking device in accordance with the present disclosure.
Figure 6:
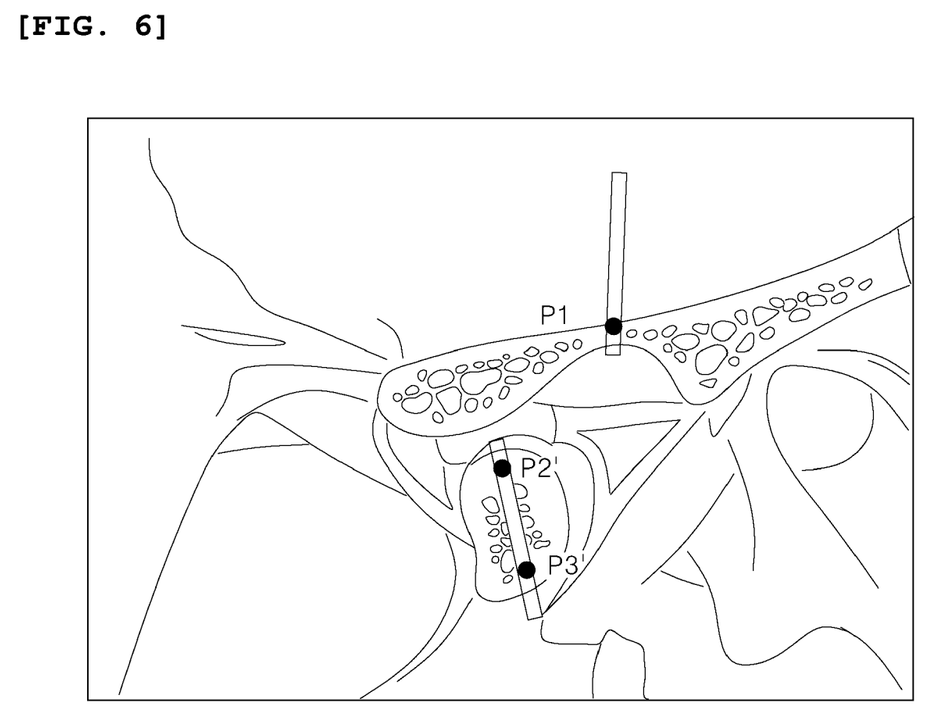
Figure 7:
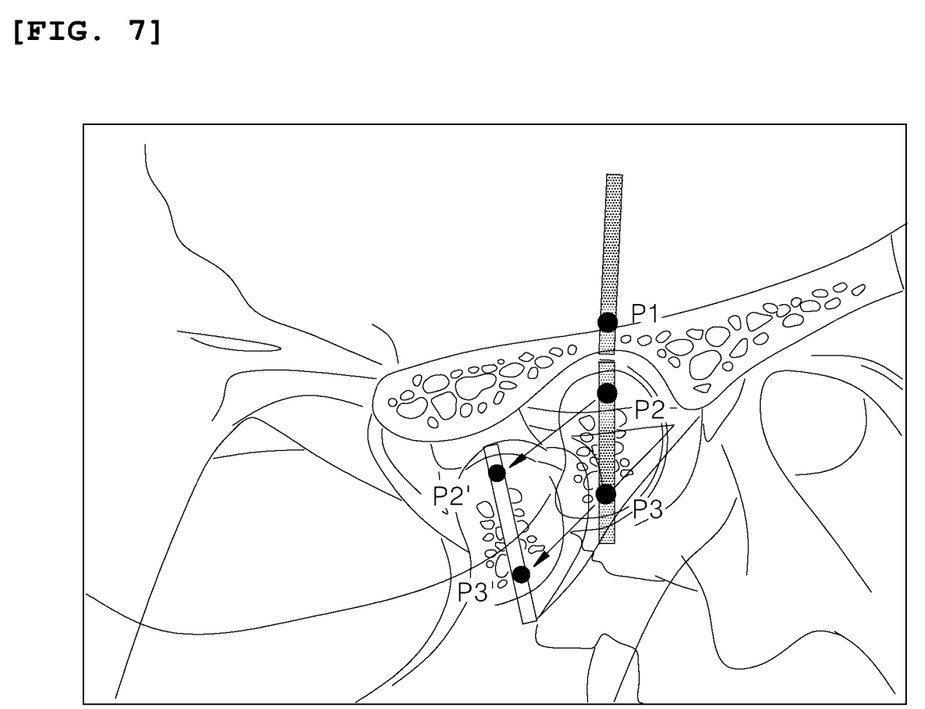

FIGS. 5 to 7 are exemplary diagrams for explaining the movement of the temporomandibular joint of the teeth movement tracking device in accordance with the present disclosure.

As illustrated in FIG. 5, a plurality of feature points P1, P2, P3 are set by distinguishing the maxilla and the mandible with respect to one axis before moving the temporomandibular joint.

As illustrated in FIG. 6, the plurality of feature points move according to the movement of the temporomandibular joint and are thus displayed on new locations. In this time, the location movements of the second feature point P2 and the third feature point P3 are largely appeared. In addition, it can be seen that the moving angles or moving distances of some of the second feature points P2 and the third feature points P3 are different. That is, it can be seen that the second feature point and the third feature point have different directionality.

FIG. 7 is a diagram for explaining the movement of the temporomandibular joint by overlapping and displaying FIGS. 5 and 6, and referring to FIG. 7, the movement directions of the second feature point and the third feature point can be confirmed, respectively.

Figure 8:
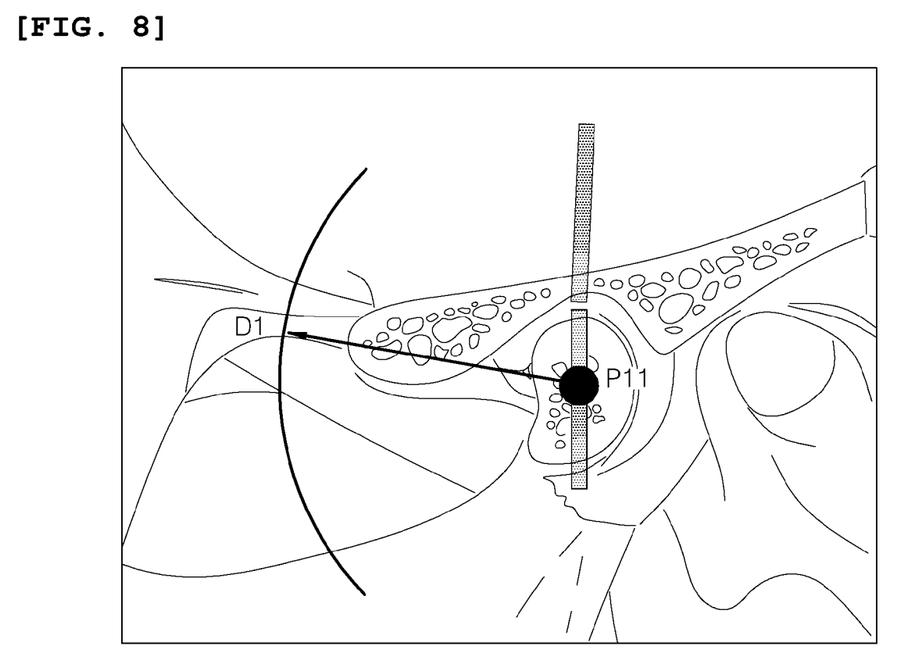
FIGS. 8 and 9 are exemplary diagrams for explaining the movement trajectory of the temporomandibular joint according to the movement of the temporomandibular joint in FIGS. 5 to 7.
Figure 9:
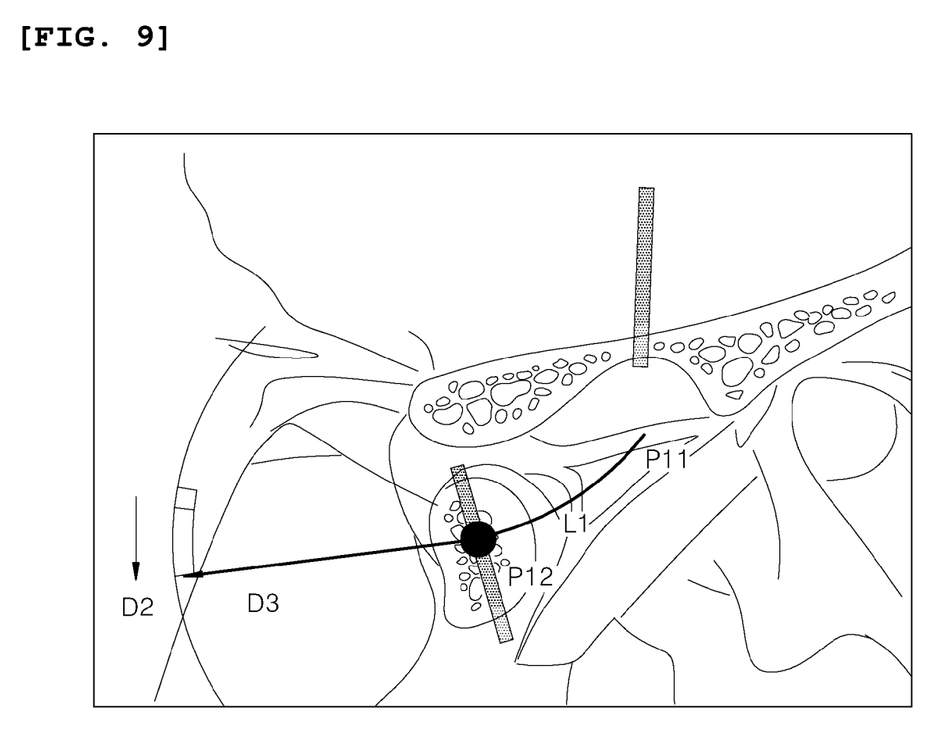

FIGS. 8 and 9 are exemplary diagrams for explaining the movement trajectory of the temporomandibular joint according to the movement of the temporomandibular joint in FIGS. 5 to 7.

As illustrated in FIG. 8, the directionality from the center P11 of the temporomandibular joint in a first direction D1 is firstly determined, and as illustrated in FIG. 9, the directionality in a second direction D2 is determined. Accordingly, the temporomandibular joint is moved along a first trajectory L1 in a third direction D3 that is the sum of the first direction D1 and the second direction D2.

The trajectory data are generated by storing the movement trajectory.

Figure 10:
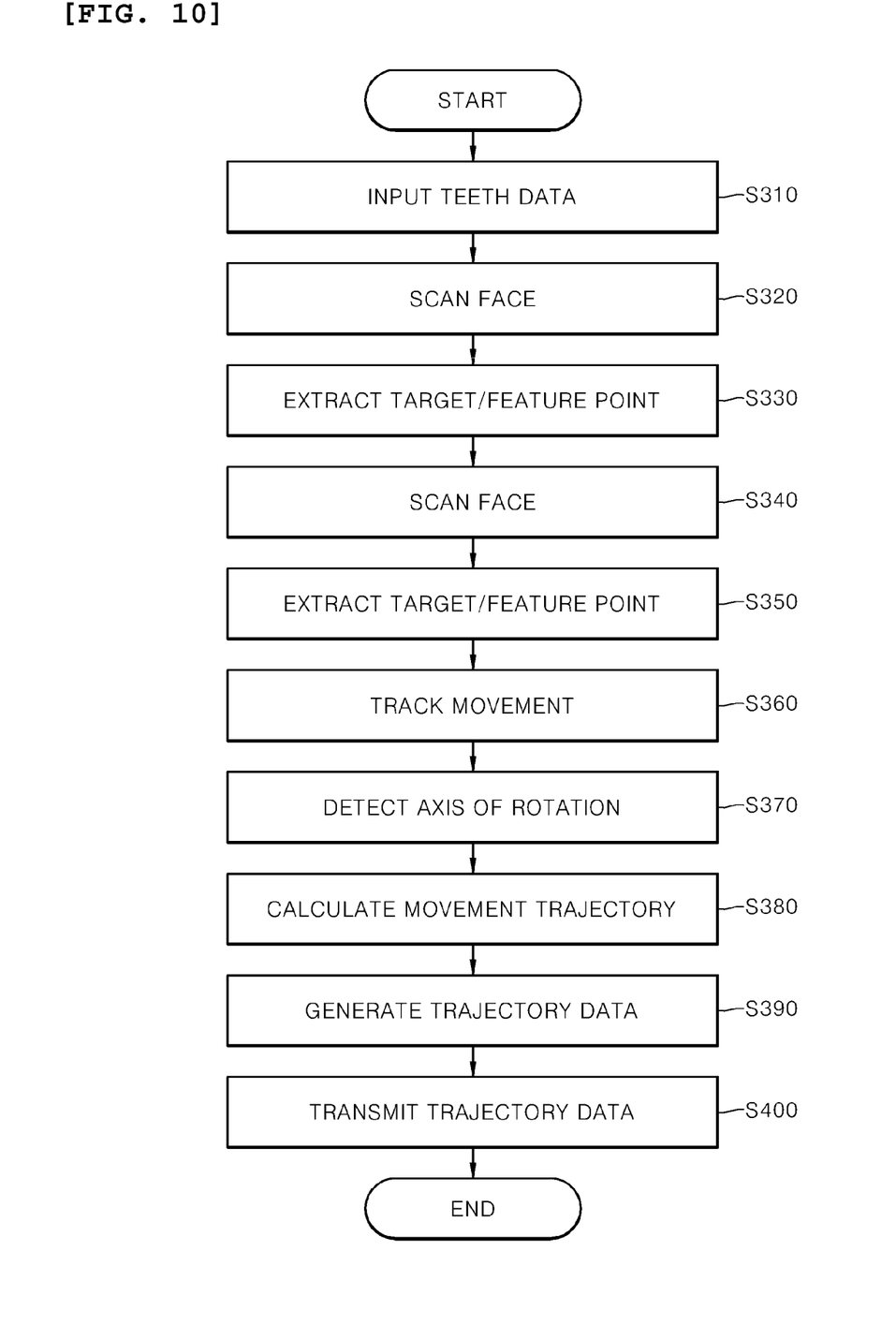
FIG. 10 is a flowchart illustrating a method for operating the teeth movement tracking device in accordance with the present disclosure.

FIG. 10 is a flowchart illustrating a method for operating the teeth movement tracking device in accordance with the present disclosure.

As illustrated in FIG. 10, teeth data are input S310. In this time, the input unit 120 can be a scanner or a three-dimensional scanner, or can be connected to the scanner or the three-dimensional scanner to receive scanned data. In addition, CT data separately photographed can be input thereto.

The scanner 130 scans a moving face S320. The image data having two or more continuity are input to the input unit 120 in real time and are processed. The image processing unit 150 can generate three-dimensional coordinate at a high speed by mapping the input three-dimensional teeth data with the image data of the face.

In this time, the image processing unit 150 uses the three-dimensional image data or the CT data of the teeth as the teeth data through two-dimensional processing. The image processing unit 150 generates three-dimensional data by combining the teeth data with the image data.

In addition, the image processing unit 150 extracts information on a target or a feature point S330.

Since a face scan is continuously performed, the extraction of the face scan S340 and the target/feature point S350 is repeatedly performed.

Meanwhile, the movement according to the movement of the teeth or the temporomandibular joint is tracked using the extracted feature point S360.

In this time, when the movement according to the movement of the target is determined or the target is not included therein, it is possible to set the feature point on the face to track the movement thereof.

The movement tracking unit 160 sets a plurality of feature points based on the three-dimensional data and tracks the movement of the respective feature points. The movement tracking unit 160 detects the axis of rotation by comparing the movement of the respective feature points to determine the feature point having the least movement S370.

The movement tracking unit 160 detects the axis of rotation of the temporomandibular joint in the section of the rotation motion of the teeth through the image data of the face having the bottom of the teeth.

The movement trajectory is calculated based on the movement of the target or the feature point with respect to the axis of rotation S380. The trajectory data are generated by connecting the movement trajectory S390. The thus generated trajectory data are transmitted to a treatment institution or a treatment device S400.

The present disclosure is not necessarily limited to these embodiments, as all the constituent elements constituting the embodiment of the present disclosure have been described as being combined and operating together. Within the scope of the present disclosure, depending on the embodiment, all of the components can operate selectively in combination with one or more.

The description above is merely illustrative of the technical idea of the present disclosure, and various modifications and changes can be made by those skilled in the art to which the present disclosure pertains without departing from the essential characteristics of the present disclosure.

According to the present disclosure, it is possible to match the teeth data with the image data scanning the moving face, and then to track the movement of the temporomandibular joint based on the moving face to generate the trajectory data, thus recording the movement of the teeth or the temporomandibular joint that is different for each person and tracking precise movement thereof. As a result, it is possible to manufacture the teeth movement tracking device capable of performing accurate diagnosis in diagnosis and treatment.

The invention claimed is:

1. A teeth movement tracking device, comprising:
an input unit for receiving three-dimensional teeth data and image data having a shape of teeth;
an image processing unit for combining the three-dimensional teeth data with the image data;
a movement tracking unit for detecting an axis of rotation of a temporomandibular joint with respect to a rotation of the teeth or the temporomandibular joint by analyzing the image data or the three-dimensional teeth data; and
a trajectory generation unit for calculating a movement trajectory of the teeth or the temporomandibular joint by analyzing the image data or the three-dimensional teeth data,
wherein the image processing unit converts all or part of the image data into three-dimensional data, using a plurality of feature points or a plurality of attached targets on the image data,
wherein the movement tracking unit detects the axis of rotation of the temporomandibular joint by comparing movements of the plurality of feature points or the plurality of attached targets and determining a feature point or an attached target, having a least movement in the three-dimensional teeth data or the image data among the plurality of feature points or the plurality of attached targets, as the axis of rotation of the temporomandibular joint.

2. The teeth movement tracking device of claim 1, wherein the image processing unit aligns the three-dimensional teeth data with the image data and synchronizes a movement thereof.

3. The teeth movement tracking device of claim 1, wherein the input unit receives the image data having two or more continuity.

4. A teeth movement tracking device, comprising:
an input unit for receiving three-dimensional teeth data and image data having a shape of teeth;
an image processing unit for combining the three-dimensional teeth data with the image data;
a movement tracking unit for detecting an axis of rotation of a temporomandibular joint with respect to a rotation of the teeth or the temporomandibular joint by analyzing the image data or the three-dimensional teeth data; and
a trajectory generation unit for calculating a movement trajectory of the teeth or the temporomandibular joint by analyzing the image data or the three-dimensional teeth data,
wherein the movement tracking unit detects the axis of rotation of the temporomandibular joint based on movements of a plurality of feature points or a plurality of attached targets on the image data, by tracking the movements of the plurality of feature points or the plurality of attached targets and determining a feature point or an attached target, having a least movement among the plurality of feature points or the plurality of attached targets, as the axis of rotation of the temporomandibular joint.

5. The teeth movement tracking device of claim 1, wherein the trajectory generation unit tracks the rotation or free motion of the teeth or the temporomandibular joint with respect to the axis of rotation of the temporomandibular joint detected by the movement tracking unit.

6. A teeth movement tracking method, comprising:
receiving three-dimensional teeth data and image data having a shape of teeth by scanning a face;
combining the three-dimensional teeth data with the image data, including converting all or part of the image data into three-dimensional data using a plurality of feature points or a plurality of attached targets on the image data;
detecting an axis of rotation of a temporomandibular joint with respect to a rotation of the teeth or temporomandibular joint based on movements of the plurality of feature points or a plurality of attached targets, by analyzing the image data or the three-dimensional teeth data for tracking the movements of the plurality of feature points or the plurality of attached targets in the three-dimensional teeth data or the image data and determining a feature point or an attached target, having a least movement in the three-dimensional teeth data or the image data among the plurality of feature points or the plurality of attached target, as the axis of rotation of the temporomandibular joint; and calculating a movement trajectory of the teeth or the temporomandibular joint by analyzing the image data or the three-dimensional teeth data.

7. The teeth movement tracking method of claim 6, wherein the receiving the image data inputs the image data having two or more continuity.

8. The teeth movement tracking method of claim 6, wherein the combining the three-dimensional teeth data with the image data aligns the three-dimensional teeth data with the image data and synchronizes a movement thereof.

9. The teeth movement tracking method of claim 6, wherein the calculating the movement trajectory tracks the rotation or free motion of the teeth or the temporomandibular joint with respect to the detected axis of rotation.

* * * * *